United States Patent
Huppert et al.

(10) Patent No.: US 10,835,660 B2
(45) Date of Patent: Nov. 17, 2020

(54) DIALYSIS SOLUTION

(71) Applicant: FRESENIUS MEDICAL CARE DEUTSCHLAND GMBH, Bad Homburg (DE)

(72) Inventors: Jochen Huppert, Saarbruecken (DE); Pascal Mathis, Bous (DE); Robert Berlich, St. Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 15/512,789

(22) PCT Filed: Sep. 15, 2015

(86) PCT No.: PCT/EP2015/001845
§ 371 (c)(1),
(2) Date: Mar. 20, 2017

(87) PCT Pub. No.: WO2016/041634
PCT Pub. Date: Mar. 24, 2016

(65) Prior Publication Data
US 2017/0296729 A1    Oct. 19, 2017

(30) Foreign Application Priority Data
Sep. 18, 2014   (DE) .................. 10 2014 013 885

(51) Int. Cl.
*A61K 33/00*  (2006.01)
*A61M 1/16*  (2006.01)
*A61K 33/06*  (2006.01)
*A61K 33/42*  (2006.01)
*A61K 9/08*  (2006.01)
*A61M 1/28*  (2006.01)
*A61K 33/10*  (2006.01)

(52) U.S. Cl.
CPC .............. *A61M 1/1654* (2013.01); *A61K 9/08* (2013.01); *A61K 33/00* (2013.01); *A61K 33/06* (2013.01); *A61K 33/42* (2013.01); *A61M 1/287* (2013.01); *A61K 33/10* (2013.01)

(58) Field of Classification Search
None
See application file for complete search history.

(56) References Cited

U.S. PATENT DOCUMENTS

2010/0206753 A1* 8/2010 Oda .................. A61K 9/0019
206/221

FOREIGN PATENT DOCUMENTS

| EP | 2206504 | 7/2010 |
| EP | 2324835 | 5/2011 |
| WO | WO 00/64456 | 11/2000 |
| WO | WO 2014/177630 | 11/2014 |

OTHER PUBLICATIONS

Ebah et al. Phophate enrichment of dialysate for use in standard and extended haemodialysis. Blood Purification, 2012, vol. 34, S. 28-33.

* cited by examiner

*Primary Examiner* — David J Blanchard
*Assistant Examiner* — Daniel F. Coughlin
(74) *Attorney, Agent, or Firm* — Jacobson Holman PLLC

(57) ABSTRACT

The present invention relates to a dialysis solution containing bicarbonate, calcium and phosphate, wherein the dialysis solution contains phosphate having a concentration in the range from up to 0.4 mmol/l, preferably in the range from up to 0.375 mmol/l, or in the range from up to 0.25 mmol/l, and particularly preferably in the range from up to 0.2 mmol/l.

13 Claims, 3 Drawing Sheets

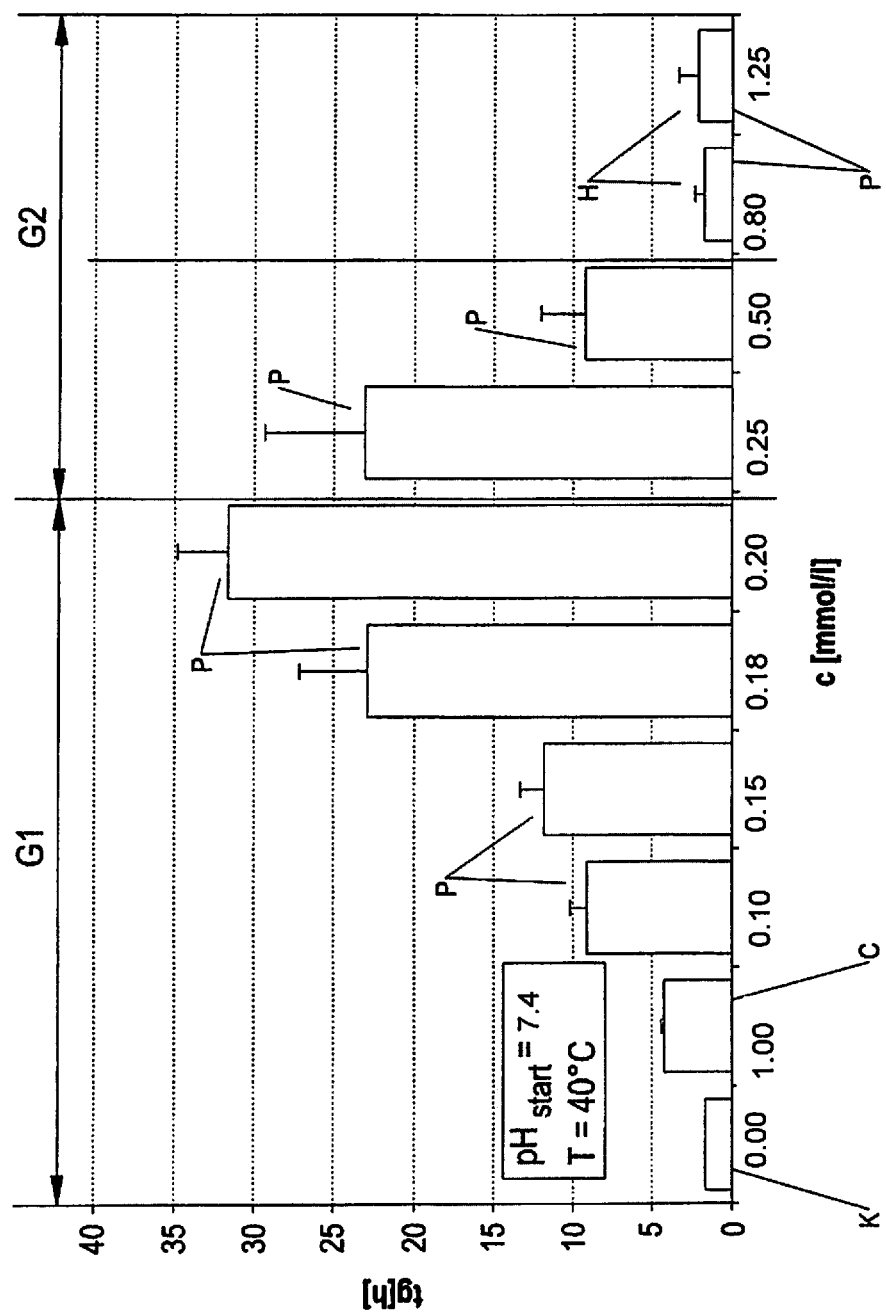

DIALYSIS SOLUTION

Figure 1:
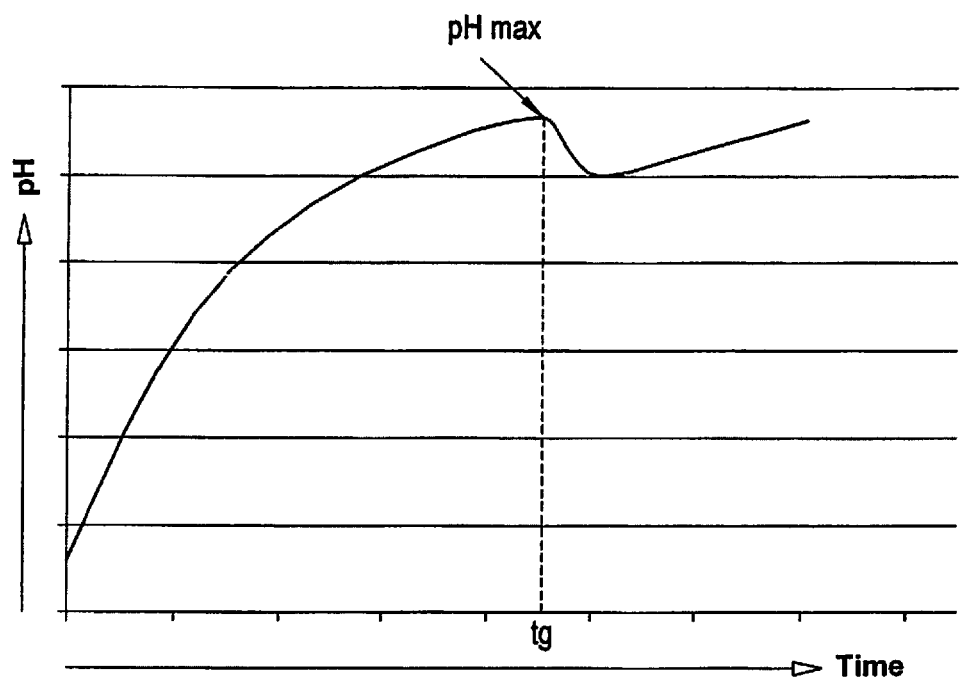

The present invention relates to a dialysis solution which contains bicarbonate, calcium and phosphate.

Bicarbonate-buffered dialysis solutions containing calcium typically contain electrolytes, buffers and glucose in physiologically effective concentrations.

It is known from the prior art to provide these solutions in the form of individual solutions which are received in a twin-chamber bag. A ready-to-use dialysis solution is obtained by mixing the two chamber contents.

There is a problem with dialysis solutions which also contain bicarbonate as a buffer in addition to calcium or magnesium in that under certain conditions, in particular at a comparatively high pH and at higher temperatures, carbonates may be formed which are of low solubility, which is unwanted. A pH increase due to a loss of $CO_2$ by degasing is in particular responsible for the precipitation reactions.

Under thermodynamic aspects, there is a maximum pH up to which the dialysis solution remains stable, i.e. up to which the named precipitations do not occur. If the pH of the dialysis solution increases under conditions of use such as by the pumping and heating at a dialysis machine, a metastable state can be achieved. If this state collapses, carbonates are precipitated which are of low solubility, which can result in considerable complications in the treatment. In this respect, magnesium carbonate and calcium carbonate represent the most critical compounds due to the poor solubility in the basic conditions.

A separate storage of calcium, on the one hand, and of hydrogen carbonate, on the other hand, and thus an increased stability in the storage of the dialysis solution, can be achieved by the provision of the individual solutions in a twin-chamber bag. It is further known from the prior art to manufacture the bag film from a high-barrier film to counteract the escape of $CO_2$ and thus the increase in the pH in the individual solution containing bicarbonate.

Nevertheless, despite this special packaging, the pH of the dialysis solution containing bicarbonate increases over the storage time, which has the consequence that on the mixing of the two individual solutions, the pH of the mixed solution, i.e. of the finished dialysis solution before its use, is likewise increased.

To avoid precipitations in the mixing or on the use at the dialysis machine, it must be ensured that the pH of the dialysis solution containing bicarbonate and the pH of the mixture manufactured from the individual solutions lie within a relatively narrow framework.

It is thus the underlying object of the present invention to further develop a dialysis solution of the initially named kind such that the probability of the occurrence of precipitations is reduced with respect to known dialysis solutions.

This object is achieved by a dialysis solution having the features of claim 1. Provision is accordingly made that the dialysis solution contains phosphate having a concentration in the range from up to 0.4 mmol/l, preferably in the range from up to 0.375 mmol/l, or in the range from up to 0.25 mmol/l, and particularly preferably in the range from up to 0.2 mmol/l.

The presence of phosphate impedes the precipitation of calcium carbonate, with it being presumed that the adsorption of a $CaHPO_4(aq)$ complex at the surface of calcium carbonate results in a blockage of the so-called active crystal growth sites.

The stability of the dialysis solution and of individual solutions from which the dialysis solution is obtained is significantly increased by the presence of phosphate in the concentration ranges named in claim 1, which is due to the fact that the collapse of the metastable region is delayed or is completely prevented. A dialysis solution safe in application over the complete life cycle of the product, preferably over a period of 24 months or longer, can thus be ensured.

It is pointed out at this point that the term "dialysis solution" includes any desired solution which can be used within the framework of dialysis. Concentrates are also to be understood by it which e.g. have to be further diluted before the use in dialysis and also ready-to-use solutions which can be used as such within the framework of dialysis.

It is further pointed out that the term "phosphate" comprises the phosphate anion per se and also compounds which contain this ion such as salts or esters of phosphoric acid. The phosphate is preferably orthophosphate.

The stabilization of the dialysis solution or of the individual solutions named below thus takes place by addition of phosphate, whereby the upper pH limit at which a precipitation of calcium carbonate takes place, is shifted further into the basic conditions, i.e. towards higher pH values. Any precipitation reactions then only take place at pH values which are so high they are usually not reached during the dialysis treatment or during the storage of the dialysis solution.

This not only results in an increased storage time, but also in a substantial gain in security on the use of the dialysis solution at a dialysis machine.

Due to the fact that the phosphate concentration lies below physiological concentration values, the medical efficacy of the dialysis solution is not influenced.

In a preferred embodiment of the invention, the dialysis solution contains phosphate in a range from 0.05 mmol/l to 0.25 mmol/l, in particular up to 0.20 mmol/l.

The lower limit of the concentration of phosphate in the dialysis solution preferably lies at 0.05 mmol/l.

The dialysis solution preferably contains electrolytes and optionally a carbohydrate compound which is preferably glucose.

Provision is made in a further embodiment of the invention that the dialysis solution contains one or more of sodium, potassium, calcium, magnesium and chloride. The naming of elements within the framework of the present invention relates to their ions.

The invention further relates to a combination of several, preferably of exactly two, individual solutions which are configured such that they form a dialysis solution in accordance with one of the claims 1 to 5 after their mixing with one another.

Provision can be made in this respect that only one of the individual solutions contains phosphate.

The phosphate can generally be present in the form of dihydrogen phosphate, for example.

A further preferred embodiment of the invention comprises one of the individual solutions containing calcium and another individual solution, which does not contain calcium, containing phosphate. Calcium and the phosphate are preferably stored separately from one another. Furthermore, calcium and hydrogen carbonate are preferably stored separately from one another, i.e. are present in different individual solutions.

In a preferred embodiment of the invention, phosphate and hydrogen carbonate are present in one and the same individual solution. In a further preferred embodiment, phosphate and hydrogen carbonate are not contained in any further individual solution.

Provision is made in a further embodiment of the invention that a first individual solution contains calcium and/or magnesium and/or chloride and/or glucose and/or potassium and a second individual solution contains sodium and/or chloride and/or hydrogen carbonate and/or phosphate. The first individual solution preferably contains neither phosphate nor hydrogen carbonate. Sodium is also only present in the second individual solution in an embodiment. The second solution preferably contains neither calcium nor magnesium. The second individual solution preferably does not contain any potassium and/or glucose.

Calcium can, for example, be present in an individual solution in a concentration range from 20 mmol/l to 40 mmol/l, and preferably at 30 mmol/l; magnesium can be present in an individual solution in a concentration range from 5 mmol/l to 15 mmol/l, and preferably at 10 mmol/l; potassium can, for example, be present in an individual solution in a concentration range from 0 mmol/l to 100 mmol/l; sodium can, for example, be present in an individual solution in a concentration range from 100 mmol/l to 200 mmol/l, and preferably at 140 mmol/l to 160 mmol/l, and preferentially at 147.5 mmol/l; hydrogen carbonate can, for example, be present in an individual solution in a concentration range from 30 mmol/l to 50 mmol/l, and preferably at 37 mmol/l; phosphate can, for example, be present in an individual solution in a concentration range from 0.05 mmol/l to 0.15 mmol/l, and preferably at 0.11 mmol/l; glucose can, for example, be present in an individual solution in a concentration range from 100 mmol/l to 120 mmol/l, and preferably at 111 mmol/l; and chloride can be present in both individual solutions.

In this respect, the chloride concentration in the individual solution which contains glucose can lie in a concentration range from 60 mmol/l to 100 mmol/l, and preferably at 82 mmol/l; and the chloride concentration in the individual solution which contains the phosphate can lie in a concentration range from 100 mmol/l to 120 mmol/l, and preferably at 110 mmol/l.

The mixed solution can comprise a sodium concentration in the range from 120 mol/l to 160 mmol/l and preferably of 140 mmol/l; potassium in the range from 0 to 4 mmol/l, calcium in the range from 1.0 mmol/l to 2.0 mmol/l, and preferably of 1.5 mmol/l; magnesium in the range from 0.2 mmol/l to 0.8 mmol/l, and preferably of 0.5 mmol/l: chloride in the range from 100 mmol/l to 120 mmol/l, and preferably 109 mmol/l; hydrogen carbonate in the range from 30 mmol/l to 40 mmol/l, and preferably 35 mmol/l: phosphate or dihydrogen phosphate in the range from 0.05 mmol/l to 0.15 mmol/l, and preferably 0.1 mmol/l; and glucose in the range from 0 mmol/l to 7 mmol/l, and preferably 6.5 mmol/l.

A possible composition of the individual solution and of the mixed solution manufactured therefrom results from the following table:

| [mmol/l] | Solution A [250 ml] | Solution B [4750 ml] | Mixed solution [5000 ml] |
| --- | --- | --- | --- |
| Sodium | 0 | 147.48 | 140 |
| Potassium | 0 | 0 | 0 |
| Calcium | 30 | 0 | 1.5 |
| Magnesium | 10 | 0 | 0.5 |
| Chloride | 82 | 110.42 | 109 |
| Hydrogen carbonate | 0 | 36.95 | 35 |
| Dihydrogen phosphate | 0 | 0.105 | 0.1 |
| Glucose | 111 | 0 | 5.55 |
| pH (release) | 2.40-3.00 | 7.00-7.30 | 7.00-7.25 |
| pH (end of durability) | 2.40-3.0 | 7.00-7.80 | 7.00-7.60 |

Potassium in solution A can, for example, generally be contained in a concentration of 40, 60 or 80 mmol/l; potassium concentrations in the mixed solution then result of 2, 3 or 4 mmol/l.

As can be seen from this table, the individual solution (solution B), which contains the phosphate, can be present in a larger volume than the individual solution (solution A), which contains calcium. In the example shown here, the volume of the one individual solution amounts to 4.75 l and the volume of the other individual solution to 0.25 l.

It is conceivable that the first individual solution, which contains the calcium, does not contain any hydrogen carbonate and/or any phosphate and/or any sodium.

It is furthermore conceivable that the second individual solution, which contains the phosphate, does not contain any calcium and/or any magnesium and/or any potassium and/or any glucose.

The one individual solution can have a pH in the range from 2.4 to 3.0. This individual solution is preferably the one which contains calcium, but not hydrogen carbonate.

Another individual solution containing the hydrogen carbonate can have a pH in the range from 7.0 to 7.8.

The pH of the dialysis solution which is acquired by mixing the individual solutions preferably lies in the range from 7.0 to 7.6.

The present invention furthermore relates to a multi-chamber bag comprising at least two chambers, wherein one of the chambers has an individual solution of the combination in accordance with one of the claims 6 to 12 and another chamber has an individual solution of the combination in accordance with one of the claims 6 to 12.

Provision is made in a preferred embodiment of the invention that the multi-chamber bag has at least one seam or another separating means which separates two chambers from one another, wherein the seam or the other separating means can preferably be opened by pressure on one of the chambers.

Further details and advantages of the invention will be explained in more detail with reference to an embodiment shown in the drawing.

Figure 2:
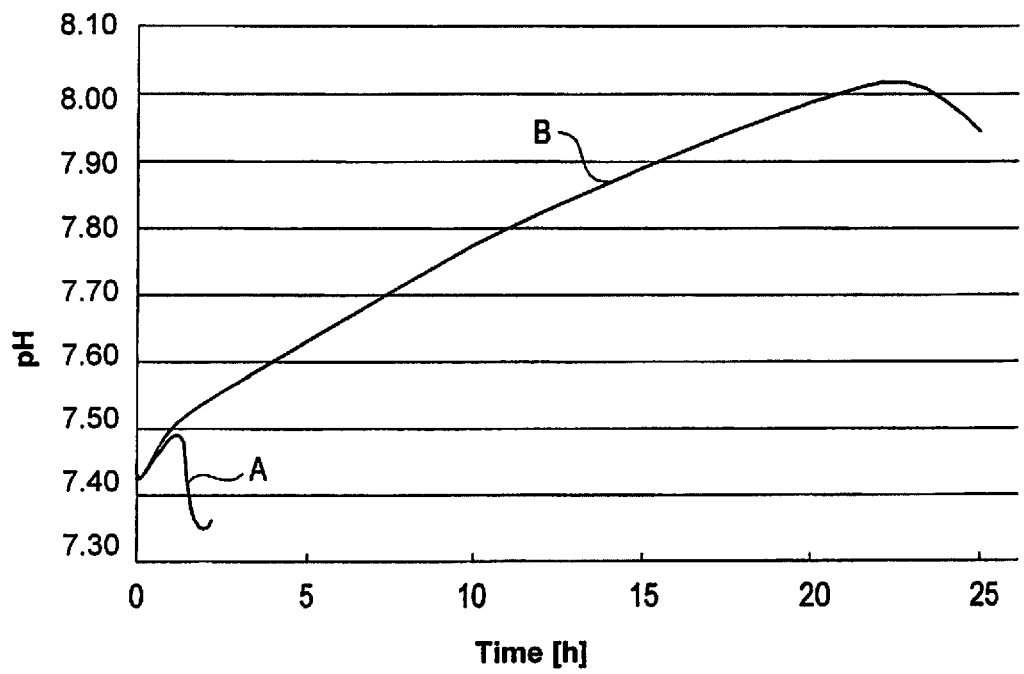
Figure 3:
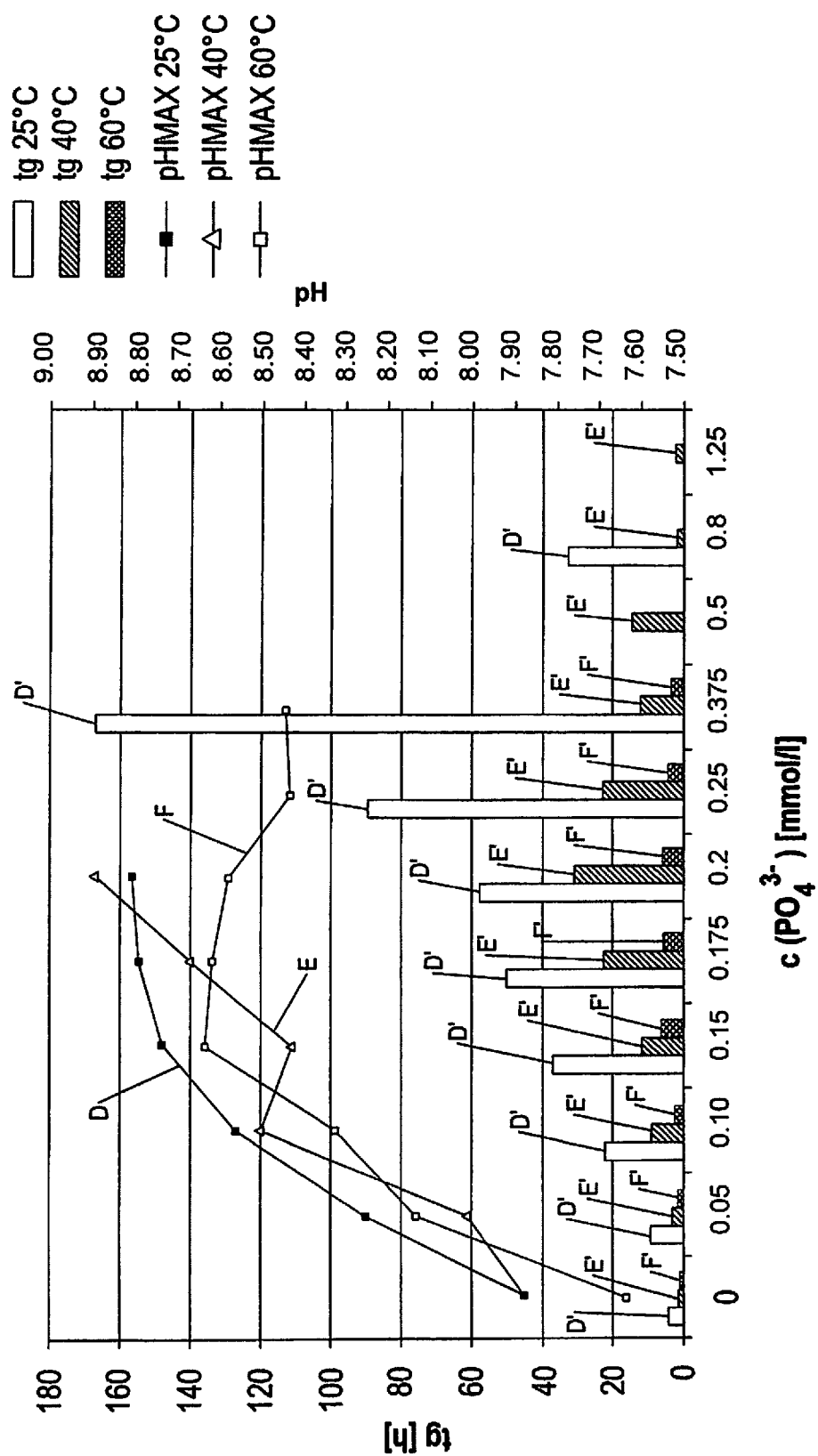

There are shown:

FIG. 1: pH development of a dialysis solution over time with a pH increase by degasing $CO_2$;

FIG. 2: pH development of a dialysis solution with and without phosphate over time with a pH increase by degasing $CO_2$;

FIG. 3: dependence of the duration of the precipitation of calcium carbonate and of the pH of the dialysis solution on the precipitation of calcium carbonate on the phosphate concentration of the dialysis solution; and FIG. 4: dependence of the duration or the precipitation of calcium carbonate on the phosphate concentration of the dialysis solution without any addition of citrate or phosphate, with the addition of citrate and with the addition of phosphate.

FIG. 1 shows the time development of the pH of a dialysis solution over time during the degasing of $CO_2$ from the dialysis solution.

The "rapid controlled precipitation method" of the "critical pH method" can be used for determining the stability of the dialysis solution, as is described in F. Hui et al: Journal European of Water Quality (Journal Européen d'Hydrologie) T.33 Fasc. 1 (2002).

The results described within the framework of this invention were obtained by a modified rapid controlled precipitation method. The experiment setup comprises 6 3-neck flasks (Carousel-6 from Radleys) which are open toward the top to ensure a uniform degasing of $CO_2$ from the solution. Furthermore, this setup allows an in-line measurement of e.g. the pH and the conductivity as well as the simultaneous heating of the flasks.

The basic principle of the method used comprises the pH of the mixed solution or of the dialysis solution being slowly raised by controlled degasing of $CO_2$ until the dialysis solution reaches a metastable state. This can be seen up to the time tg in FIG. 1.

If the dialysis solution collapses due to precipitation of calcium carbonate, this can be detected by a drop in the pH and in the conductivity. Directly after this in time, a white deposition can be visually observed. The maximum pH, which is marked as "pH max" in FIG. 1, up to which no precipitations occur is considered the characteristic for the stability of a dialysis solution.

As stated, the time tg (time of germination) is the first measurement point at which a drop in the pH is detected.

In FIG. 1, the increase in the pH up to the time tg can be explained by the degasing of $CO_2$ from the dialysis solution. As can furthermore be seen from FIG. 1, a local pH maximum arises. After this point, oversaturation of the dialysis solution occurs and a precipitation of calcium carbonate takes place. Carbonate ions are removed from the dialysis solution on the precipitation. The pH drops and protons are increasingly formed due to the equilibrium reaction with hydrogen carbonate, which results in the drop in the pH.

The stability of the dialysis solution or of an individual solution can be significantly increased by the addition of phosphate or of orthophosphate, with the collapse of the metastable range being delayed or prevented in full.

This can be seen from FIG. 2. This Figures shows as the line A the pH development of a dialysis solution containing sodium, calcium, magnesium, chloride, hydrogen carbonate and glucose, but without phosphate, over time. Line B shows the pH development of an identical dialysis solution which, as the only difference, contains 0.1 mmol/l phosphate.

The experiment on which FIG. 2 is based was carried out with a filling volume of 275 ml and the 3-neck flasks were closed by diaphragms having openings of 3 mm in diameter to control the degasing of $CO_2$. The experiment was carried out with a starting pH of 7.4 and at a temperature of 60° C.

As can be seen from the development in accordance with line A, the pH initially increases up to a maximum value of 7.47. The pH then falls due to the precipitation of calcium carbonate. This takes place at a time of 45 min after the start of the experiment, i.e. tg=45 min.

Line B shows that the addition of phosphate has a substantial effect on the pH. The maximum achievable pH amounts to 8.02 and the length of time up to the occurrence of the precipitation of calcium carbonate amounts to around 22 hours. This means that not only the pH at which a calcium carbonate precipitation takes place, but also the time interval until this precipitation occurs is increased by the presence of phosphate.

The effect of phosphate as a means stabilizing the dialysis solution is dependent on the temperature and on the concentration.

FIG. 3 shows the developments of the maximum pH, i.e. of the pH which is measured on the start of the precipitation, as well as the time interval (tg) which elapses from the start of the experiment to the precipitation. The experiments were carried out using the experiment setup described in FIG. 1.

As can be seen from FIG. 3, the stabilizing effects of orthophosphate are dependent on the temperature and on the concentration. The stability of the dialysis solutions significantly depends on the phosphate concentration, which is expressed both in the respectively reached pH max values, i.e. in the maximum pH values, up to which the dialysis solutions are stable, and in the tg values, i.e. in the time intervals which elapse from the experiment start until the precipitation starts and the pH falls again.

In FIG. 3, the lines D, E and F are the developments of the pH max values for a solution temperature of 25° C. (line D), 40° C. (line E) and 60° C. (line F).

A temperature dependence of the stabilization effect furthermore clearly results from FIG. 3. It can thus be easily recognized from FIG. 3 that, for example, at a temperature of 25° C. (columns D'), a dialysis solution with a phosphate content of 0.375 mmol/l has the greatest stability; but at a temperature of 40° C. (columns E'), a dialysis solution having a phosphate content of 0.2 mmol/l is the most stable. At a temperature of 60° C. (columns F'), a dialysis solution having a phosphate concentration of 0.15 mmol/l shows the greatest stability.

FIG. 4 shows the concentration dependence of the stabilizing effect by way of example for a solution temperature of 40° C.

As can be seen from FIG. 4 and in agreement with FIG. 3, a stability maximum is reached at this temperature with a phosphate concentration of 0.2 mmol/l. The dialysis solutions containing phosphate are marked by the letter P. At this temperature, the stability of the dialysis solution drops again with a further increase in the phosphate concentration, which can be recognized by the fact that the time interval tg up to the precipitation again becomes smaller.

The fall in the stability of the dialysis solution at the named temperature of 40° C. from a phosphate concentration of 0.2 mmol/l is due to the fact that calcium phosphates of low solubility are formed.

No calcium phosphate precipitation can be observed in the range G1; in contrast, a calcium phosphate precipitation occurs in the range G2.

It can furthermore be seen from FIG. 4 that an addition of citrate (c=1 mmol/l; no phosphate) (letter C) admittedly effects a certain stabilization of the dialysis solution in comparison with a dialysis solution without stabilization means (letter K), but that the stabilizing effect is much more pronounced in the case of phosphate.

A dialysis solution having 0.1 mmol/l phosphate is thus stable for around twice as long as a dialysis solution having 1 mmol/l citrate under the above named experiment conditions.

It further results from FIG. 4 that a concentration of phosphate in the medically relevant range from 0.8 mmol/l to 1.25 mmol/l (letter H) with an otherwise analog solution composition does not have any increased stability.

In summary, it can thus be stated that the addition of phosphate or of orthophosphate in the claimed concentration ranges results in a significant increase in the stability of bicarbonate-buffered dialysis solutions containing calcium. The probability of precipitation reactions can be substantially reduced, which considerably increases the safety and the durability of dialysis solutions without influencing the medical efficacy.

The small phosphate concentrations in accordance with the invention have no medical efficacy so that the dialysis solutions can be used easily within the framework of the dialysis.

The invention claimed is:

1. A two-chamber bag comprising first and second chambers holding first and second individual solutions, respectively, which first and second individual solutions are configured to form a ready-to-use dialysis solution upon mixing with one another, wherein the first individual solution contains calcium, magnesium, and chloride, does not contain sodium, and has a pH in the range of 2.4 to 3.0, the second individual solution contains sodium, chloride, bicarbonate, and phosphate, has a volume greater than the first individual solution, and has a pH in the range of 7.0 to 7.8, and the ready-to-use dialysis solution contains the phosphate in a concentration of up to 0.4 mmol/l, the calcium, and the bicarbonate.

2. A bag in accordance with claim 1, characterized in that the dialysis solution contains the phosphate in a concentration range from 0.05 mmol/l to 0.25 mmol/l.

3. A bag in accordance with claim 1, characterized in that the dialysis solution comprises the phosphate in a concentration of 0.05 mmol/l-0.4 mmol/l.

4. A bag accordance with claim 1, characterized in that the dialysis solution further contains electrolytes and at least one osmotic agent or at least one carbohydrate compound.

5. A bag in accordance with claim 1, characterized in that the first individual solution further does not contain at least one of hydrogen carbonate and phosphate.

6. A bag in accordance with claim 1, characterized in that the second individual solution does not contain at least one of calcium, magnesium, potassium, and glucose.

7. A bag in accordance with claim 1 further comprising a separating means which separates the two chambers from one another, wherein the separating means is opened by pressure on one of the chambers.

8. A bag in accordance with claim 1 further comprising a seam which separates the two chambers from one another, wherein the seam is opened by pressure on one of the chambers.

9. A bag in accordance with claim 1, characterized in that the dialysis solution contains the phosphate in a concentration of up to 0.375 mmol/l.

10. A bag in accordance with claim 1, characterized in that the dialysis solution contains the phosphate in a concentration of up to 0.25 mmol/l.

11. A bag in accordance with claim 1, characterized in that the dialysis solution contains the phosphate in a concentration of up to 0.2 mmol/l.

12. A bag in accordance with claim 1, characterized in that the dialysis solution further contains electrolytes and at least one osmotic agent or glucose.

13. A bag in accordance with claim 1, characterized in that the dialysis solution further contains electrolytes and at least one osmotic agent or glucose.

* * * * *